United States Patent
Jung et al.

(10) Patent No.: US 6,780,953 B2
(45) Date of Patent: Aug. 24, 2004

(54) ORGANIC POLYMER FOR ANTI-REFLECTIVE COATING LAYER AND PREPARATION THEREOF

(75) Inventors: Min-Ho Jung, Gyunggi-do (KR); Sung-Eun Hong, Gyunggi-do (KR); Ki-Ho Baik, Gyunggi-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 10/293,022

(22) Filed: Nov. 12, 2002

(65) Prior Publication Data

US 2003/0118736 A1 Jun. 26, 2003

Related U.S. Application Data

(63) Continuation of application No. 09/750,232, filed on Dec. 27, 2000, now abandoned.

(30) Foreign Application Priority Data

Dec. 30, 1999 (KR) .............................................. 99-65675

(51) Int. Cl.[7] .......................... C08F 220/68; G03C 5/00
(52) U.S. Cl. ................... 526/320; 526/318.1; 526/319; 526/329.2; 526/348.3; 430/325; 430/326; 430/330; 430/272.1; 430/270.1; 430/311
(58) Field of Search ............................... 526/320, 319, 526/318.1, 329.2, 348.3; 430/325, 326, 311, 330, 270.1, 272.1

(56) References Cited

U.S. PATENT DOCUMENTS

| | | |
|---|---|---|
| 4,424,270 A | 1/1984 | Erdmann et al. |
| 4,522,856 A | 6/1985 | Paisley et al. |
| 4,822,718 A | 4/1989 | Latham et al. |
| 5,290,894 A | 3/1994 | Melrose et al. |
| 5,525,457 A | 6/1996 | Nemoto et al. |
| 5,674,648 A | 10/1997 | Brewer et al. |
| 5,939,236 A | 8/1999 | Pavelchek et al. |
| 6,190,839 B1 | 2/2001 | Pavelchek et al. |
| 6,489,432 B2 * | 12/2002 | Jung et al. .................. 528/230 |

FOREIGN PATENT DOCUMENTS

| | | |
|---|---|---|
| EP | 0 277 038 A2 | 8/1988 |
| EP | 0 813 114 A2 | 12/1997 |
| EP | 0 823 661 A1 | 2/1998 |
| EP | 0 834 770 A2 | 4/1998 |
| WO | WO00/01752 | 1/2000 |

OTHER PUBLICATIONS

Dr. H. Schulz et al., *Angew Chem*.1950, 62, 105–118.

* cited by examiner

*Primary Examiner*—Tatyana Zalukaeva
(74) *Attorney, Agent, or Firm*—Townsend and Townsend and Crew LLP

(57) ABSTRACT

The present invention provides a polymer that can be used as an anti-reflective coating (ARC) polymer, an ARC composition comprising the same, methods for producing the same, and methods for using the same. The polymer of the present invention is particularly useful in a submicrolithographic process, for example, using KrF (248 nm) or ArF (193 nm) lasers as a light source. The polymer of the present invention comprises a chromophore that is capable of absorbing light at the wavelengths used in a submicrolithographic process. Thus, the ARC of the present invention significantly reduces or prevents back reflection of light and the problem of the CD alteration caused by the diffracted and/or reflected light. The ARC of the present invention also significantly reduces or eliminates the standing wave effect and reflective notching. Therefore, the polymer of the present invention can be used to produce a stable ultrafine pattern that is suitable in manufacturing of 64M, 256M, 1G, 4G and 16G DRAM semiconductor devices. Moreover, the ARC of the present invention significantly improves the production yield of such semiconductor devices.

8 Claims, No Drawings

ORGANIC POLYMER FOR ANTI-REFLECTIVE COATING LAYER AND PREPARATION THEREOF

BACKGROUND OF THE INVENTION

1. Field of the Invention

The present invention relates to an anti-reflective polymer that is useful in a submicrolithographic process, a composition comprising the polymer, and a method for preparing the same. In particular, the present invention relates to a polymer that can be used in an anti-reflective coating layer to reduce or prevent back reflection of light and/or to eliminate the standing waves in the photoresist layer during a submicrolithographic process. The present invention also relates to a composition comprising the polymer, and a method for using the same.

2. Description of the Prior Art

In most submicrolithographic processes standing waves and/or reflective notching of the waves typically occur due to the optical properties of the lower layer coated on a substrate and/or due to changes in the thickness of a photosensitive (i.e., photoresist) film applied thereon. In addition, typical submicrolithographic processes suffer from a problem of CD (critical dimension) alteration caused by diffracted and/or reflected light from the lower layer.

One possible solution is to apply an anti-reflective coating (i.e., ARC) between the substrate and the photosensitive film. Useful ARCs have a high absorbance of the light wavelengths that are used in submicrolithographic processes. ARCs can be an inorganic an organic material, and they are generally classified as "absorptive" or "interfering" depending on the mechanism. For a microlithographic process using I-line (365 nm wavelength) radiation, inorganic anti-reflective films are generally used. Typically, TiN or amorphous carbon (amorphous-C) materials are used for an absorptive ARC and SiON materials are typically used for an interfering ARC.

SiON-based anti-reflective films have also been adapted for submicrolithographic processes that use a KrF light source. Recently, use of an organic compound as ARC has been investigated. It is generally believed that an organic compound based ARCs are particularly useful in submicrolithographic processes, in particular those using an ArF light source.

In order to be useful as an ARC, an organic compound needs to have many diverse and desirable physical properties. For example, a cured ARC should not be soluble in solvents because dissolution of the organic ARC can cause the photoresist composition layer to peel-off in a lithographic process. One method for reducing the solubility of cured ARC is to include cross-linking moieties such that when cured the ARC becomes cross-linked and becomes insoluble in most solvents used in lithographic processes. In addition, there should be minimum amount of migration (i.e., diffusion), if at all, of materials, such as acids and/or amines, to and from the ARC. If acids migrate from the ARC to an unexposed area of the positive photoresist film, the photosensitive pattern is undercut. If bases, such as amines, diffuse from the ARC to an unexposed area of the positive photoresist film a footing phenomenon occurs. Moreover, ARC should have a faster etching rate than the upper photosensitive (i.e., photoresist) film to allow the etching process to be conducted smoothly with the photosensitive film serving as a mask. Preferably, an organic ARC should be as thin as possible and have an excellent light reflection prevention property.

While a variety of ARC materials are currently available, none of these materials is useful in ArF laser submicrolithographic processes. In the absence of an ARC, the irradiated light penetrates into the photoresist film and is back reflected or scattered from its lower layers or the surface of the substrate (e.g., semiconductor chip), which affects the resolution and/or the formation of a photoresist pattern.

Therefore, there is a need for an ARC material which have a high absorbance of the wavelengths used in submicrolithographic processes.

SUMMARY OF THE INVENTION

It is an object of the present invention to provide an organic polymer that can be used as an ARC material for submicrolithography using the ArF laser (193 nm) and KrF laser (248 nm).

It is another object of the present invention to provide a method for preparing an organic polymer that reduces or prevents diffusion and/or light reflection in submicrolithography.

It is a further object of the present invention to provide an ARC composition comprising such an organic diffusion/reflection preventing or reducing polymer and a method for producing the same.

It is a still further object of the present invention to provide a method for producing a photoresist pattern with reduced standing wave effect using a submicrolithographic process.

DETAILED DESCRIPTION OF THE INVENTION

One aspect of the present invention provides an acrylate derivative polymer, an ARC composition comprising the same, and a method for using the same. In one particular embodiment, the polymer of the present invention comprises a chromophore which has a high absorbance at 193 nm and 248 nm wavelengths.

ARC compositions of the present invention can comprise a mixture polymers which include cross-linking moieties such that the polymers become cross-linked (i.e., cured) when heated (or "hard baked"). Cross-linking moieties can comprise an alcohol group and other functional group that is capable of reacting with the alcohol group to form a cross-linkage. It is believed that cross-linking of the polymer significantly improves the adhesiveness and the dissolution properties of the ARC compositions.

As will be described in more detail later, the monomer is economically favorable because of its low cost. In addition, the monomer is designed to polymerize through a simple reaction, thus being suitable for the mass production of the polymer.

Uncured polymers of the present invention are soluble in most hydrocarbon solvents; however, cured polymers are substantially insoluble in most solvents. Thus, polymers of the present invention can be easily coated onto a substrate and are capable of preventing undercutting and footing problems that can occur during a photoresist pattern formation process on photosensitive materials (i.e., photoresist compositions). Moreover, ARCs of the present invention have a higher etching rate than conventional photosensitive films resulting in an improved etching ratio between ARCs and photosensitive films, i.e., higher etching selectivity.

One embodiment of the present invention provides an ARC polymer selected from the group consisting of a polymer of the formula:

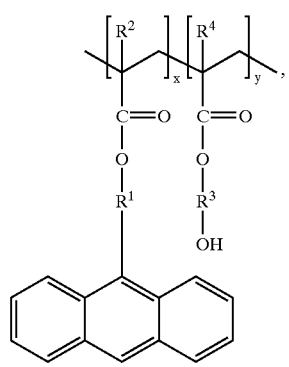

1

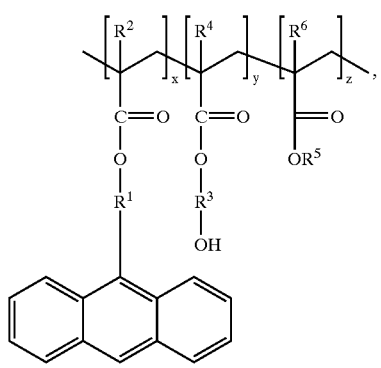

2

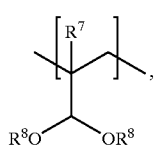

3 and mixtures thereof, wherein each of $R^1$ and $R^3$ is independently $C_1$–$C_5$ alkylene;

each of $R^2$, $R^4$ and $R^6$ is independently hydrogen or alkyl;

$R^5$ and $R^8$ are alkyl;

$R^7$ is hydrogen or alkyl;

x, y and z are mole fractions, each of which is in the range of from about 0.01 to about 0.99. Alkyl groups according to the present invention are aliphatic hydrocarbons which can be straight or branched chain groups.

Preferably $R^1$ is methylene. Preferably each of $R^2$, $R^4$ and $R^6$ is independently hydrogen or methyl. Preferably $R^5$ and $R^8$ are methyl. Preferably $R^3$ is ethylene, propylene, or butylene. Preferably $R^7$ is hydrogen or methyl, more preferably $R^7$ is hydrogen.

The polymer of Formula 1 can be prepared by polymerizing a mixture of monomers comprising a 9-anthracenealkylacrylate compound of the formula:

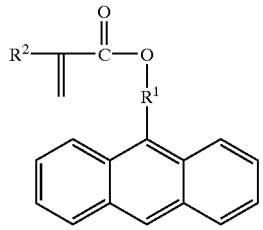

1A and a hydroxyalkylacrylate compound of the formula:

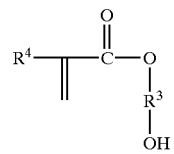

1B under conditions sufficient to produce the polymer of Formula 1, where $R^1$, $R^2$, $R^3$, and $R^4$ are those defined above. Each monomer in the mixture is present in a mole fraction amount of from about 0.01 to about 0.99.

The polymer of Formula 2 can be produced by polymerizing a mixture of monomers comprising a 9-anthracenealkyl acrylate compound of Formula 1A above, a hydroxyalkylacrylate compound of Formula 1B above, and an alkyl acrylate compound of the formula:

1C $$R^6\!-\!\!\!\!=\!\!\!\!-\overset{\overset{\displaystyle O}{\|}}{C}\!-\!OR^5$$

wherein $R^5$ and $R^6$ are those defined above. Each monomer in the mixture is present in a mole fraction amount of from about 0.01 to about 0.99.

The hydroxyalkylacrylate compound of Formula 1B and the alkylacrylate compound of Formula 1C are commercially available or can be readily prepared by those skilled in the art.

The polymer of Formula 3 can be produced by polymerizing a monomer of the formula:

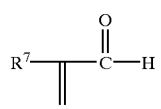

1D under conditions sufficient to produce a poly(acrolein) polymer of the formula:

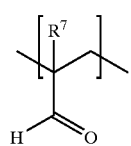

and contacting the poly(acrolein) polymer with an alcohol of the formula $R^8OH$ under conditions sufficient to produce the poly(acroleinalkylacetal) of Formula 3, wherein $R^7$ and $R^8$ are those defined above. The alcohol can be a mixture of different alcohols (e.g., each $R^8$ of the poly (acroleinalkylacetal) of Formula 3 is different) or a homogeneous alcohol system (i.e., only one type of alcohol is present). For example, a solution of (meth)acrolein in an organic solvent is polymerized in the presence of a polymerization initiator, after which the resulting polymeric product is reacted with methanol in the presence of an acid catalyst, e.g., trifluoromethylsulfonic acid.

Polymerization reactions disclosed above for preparation of polymers of Formula 1, 2, and 3 can include a polymerization initiator. Suitable polymerization initiators are well known to one of ordinary skill in the art including polymerization initiators that are used in conventional radical polymerization reactions such as 2,2,-azobisisobutyronitrile (AIBN), acetylperoxide, laurylperoxide and t-butylperoxide.

Polymerization reactions disclosed above for preparation of polymers of Formula 1, 2, and 3 can also include a polymerization solvent. Suitable polymerization solvents are well known to one of ordinary skill in the art. Exemplary polymerization solvents include organic solvents that are used in conventional polymerization reaction. Preferably, the polymerization solvent is selected from the group consisting of tetrahydrofuran, toluene, benzene, methylethyl ketone and dioxane.

Polymerization reactions disclosed above for preparation of polymers of Formula 1, 2, and 3 is preferably carried out at temperature in the range of from about 50° C. to about 90° C.

The 9-anthracenealkylacrylate compound which is useful in preparation of polymers of Formula 1 and 2 can be synthesized by reacting 9-anthracenealkyl alcohol with activated acryloyl compound, e.g., acryloylchloride or acryloyl anhydride, or other similarly activated acryloyl compounds known to one of ordinary skill in the art. Preparation of the 9-anthracenealkylacrylate compound is typically conducted in an inert organic solvent.

Another aspect of the present invention provides an ARC composition comprising the polymer of Formula 1, 2, or 3, and a method for producing the same. Yet another aspect of the present invention provides an ARC composition comprising the polymer of Formula 1 or 2 in combination with the polymer of Formula 3, and a method for producing the same.

The ARC composition of the present invention can also include an additive selected from the group consisting of anthracene, 9-anthracenemethanol, 9-anthracenecarbonitrile, 9-anthracenecarboxylic acid, dithranol, 1,2,10-anthracenetriol, anthraflavonic acid, 9-anthraldehydeoxime, 9-anthraldehyde, 2-amino-7-methyl-5-oxo-5H-[1]benzopyrono[2,3-b]pyridine-3-carbonitrile, 1-aminoanthraquinone, anthraquinone-2-carboxylic acid, 1,5-dihydroxyanthraquinone, anthrone, 9-anthryltrifluoromethyl ketone, 9-alkylanthracene derivative of the formula:

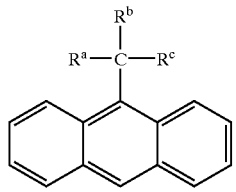

9-carboxylanthracene derivative of the formula:

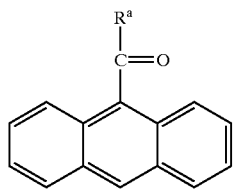

1-carboxylanthracene derivative of the formula:

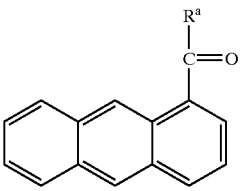

and mixtures thereof,
wherein
each of $R^a$, $R^b$, and $R^c$ is independently hydrogen, hydroxy, hydroxyalkyl, optionally substituted $C_1$–$C_5$ alkyl, or alkoxyalkyl.

In one particular embodiment of the present invention, a mixture of the polymer of Formula 3 and either the polymer of Formula 1 or 2 are combined in an organic solvent. Additive described above can be also added, typically in the amount ranging from about 0.1% by weight to about 30% by weight. The solution can optionally be filtered prior to being coated on to a substrate.

While any conventional organic solvents can be used in the ARC composition, preferred organic solvents include ethyl 3-ethoxypropionate, methyl 3-methoxypropionate, cyclohexanone, and propylene glycol methyletheracetate. The solvent is preferably used in the amount ranging from about 200 to about 5,000% by weight based on the total weight of the ARC polymers used.

Another aspect of the present invention provides a method for producing an ARC coated substrate. In one particular embodiment, a substrate (e.g., wafter) is coated with any one of the ARC composition described above. The coated substrate is then cured (i.e., heated or hard-baked) to produce the ARC coated substrate. Without being bound by any theory, it is believed that when heated the ARC polymers become cross-linked producing a film. The cross-linked structure allows the formation of the photosensitive film under optically stable exposure conditions. Preferably the coated substrate is heated to temperature in the range of from about 100 to about 300° C. for a period of from about 10 sec to about 1,000 sec.

It has been found by the present inventors that the ARCs of the present invention exhibit high performance in submicrolithographic processes, in particular using KrF (248 nm), ArF (193 nm) and $F_2$ (157 nm) lasers as light sources. In addition, the ARCs of the present invention also exhibit high performance in photolithographic processes using E-beams (157 nm), EUV (extremely ultraviolet), and ion beams as light sources.

Additional objects, advantages, and novel features of this invention will become apparent to those skilled in the art upon examination of the following examples thereof, which are not intended to be limiting.

EXAMPLE I

Synthesis of poly[9-anthracenemethylacrylate-(2-hydroxyethylacrylate)] binary copolymer Synthesis of 9-anthracenemethylacrylate To a solution of tetrahydrofuran was added 0.5 mole of 9-anthracenemethanol, 0.5 mole of pyridine, and 0.5 mole of acryloyl chloride. After completion of the reaction, the product was filtered, dissolved in ethyl acetate, washed with water, and concentrated by distillation under vacuum to give 9-anthracenemethylacrylate of Formula 7. Yield 85%.

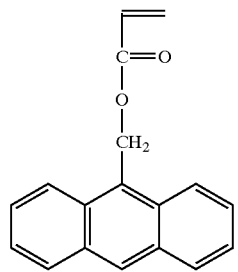

7

Synthesis of poly[9-anthracenemethylacrylate/2-hydroxyethylacrylate] copolymer

To a 500 ml round-bottom flask was added 0.5 mole of 9-anthracenemethylacrylate, 0.5 mole of 2-hydroxyethylacrylate, 300 g of tetrahydrofuran (THF), and 0.1–3 g of 2,2'-azobisisobutyronitrile (AIBN). The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylacrylate/2-hydroxyethylacrylate] polymer of the Formula 12. Yield: 82%.

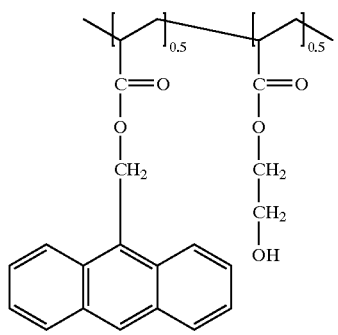

8

EXAMPLE II

Synthesis of poly[9-anthracenemethylacrylate/3-hydroxypropylacrylate] copolymer

To a 500 ml round-bottom flask was added 0.5 mole of 9-anthracenemethylacrylate (prepared according to the procedure of Example I), 0.5 mole of 3-hydroxypropylacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to produce poly[9-anthracenemethylacrylate/3-hydroxypropylacrylate] copolymer of the Formula 9. Yield: 83%.

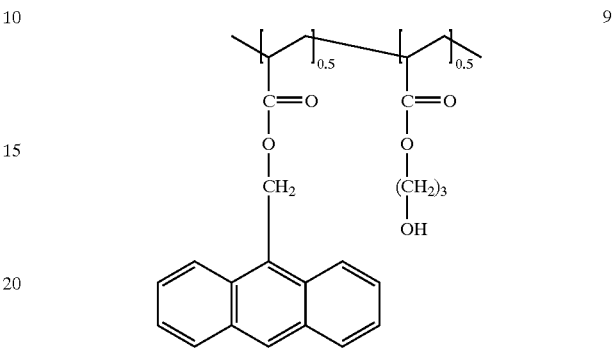

9

EXAMPLE III

Synthesis of poly[9-anthracenemethylacrylate/4-hydroxybutylacrylate] copolymer

To a 500 ml round-bottom flask was added 0.5 mole of 9-anthracenemethylacrylate, 0.5 mole of 4-hydroxybutylacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylacrylate/4-hydroxybutylacrylate] copolymer of Formula 10. Yield: 80%.

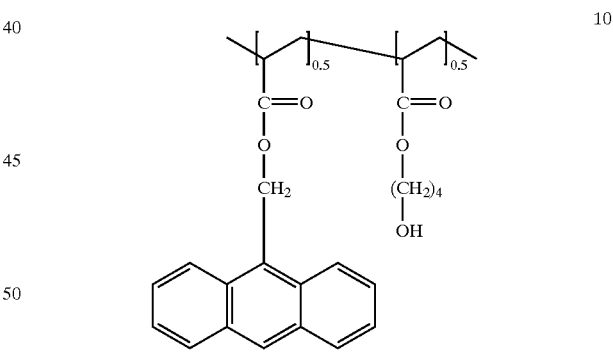

10

EXAMPLE IV

Synthesis of poly[9-anthracenemethylmethacrylate/2-hydroxyethylacrylate] copolymer Synthesis of 9-anthracenemethylmethacrylate To a solution of THF was added 0.5 mole of 9-anthracene methanol, 0.5 mole of pyridine, and 0.5 mole of methacryloyl chloride. After completion of the reaction, the product was filtered, dissolved in ethyl acetate, washed with water, and concentrated by distillation under vacuum to afford 9-anthracenemethylmethacrylate of Formula 11. Yield: 83%.

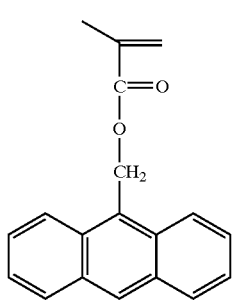

Synthesis of poly[9-anthracenemethylmethacrylate/
2-hydroxyethylacrylate] copolymer To a 500 ml round-bottom flask was added 0.5 mole of 9-anthracenemethylmethacrylate, 0.5 mole of 2-hydroxyethylacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylmethacrylate/2-hydroxyethylacrylate] copolymer of Formula 12. Yield: 79%.

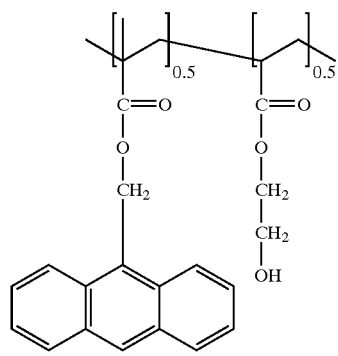

EXAMPLE V

Synthesis of poly[9-anthracenemethylmethacrylate/
3-hydroxypropylacrylate] copolymer To a 500 ml round-bottom flask was added 0.5 mole of 9-anthracenemethylmethacrylate, 0.5 mole of 3-hydroxypropylacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylmethacrylate/3-hydroxypropylacrylate] copolymer of Formula 13. Yield: 85%.

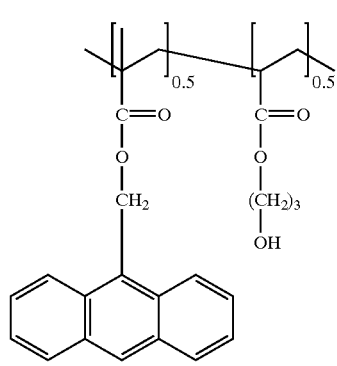

EXAMPLE VI

Synthesis of poly[9-anthracenemethylmethacrylate/
4-hydroxybutylacrylate] copolymer To a 500 ml round-bottom flask was added 0.5 mole of 9-anthracenemethylmethacrylate, 0.5 mole of 4-hydroxybutylacrylate, 300 g of THF, and 0.1–3 g of AIBN. The resulting solution was stirred at 60–75°C. for 5–20 hours under nitrogen atmosphere. The reaction mixture was precipitated in ethyl ether or n-hexane. The precipitate was filtered and dried to provide poly[9-anthracenemethylmethacrylate/4-hydroxybutylacrylate] copolymer of Formula 14. Yield: 82%.

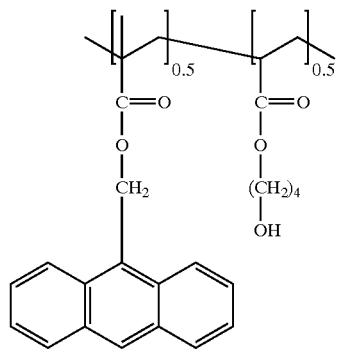

EXAMPLE VII

Synthesis of poly[9-anthracenemethylacrylate/2-
hydroxyethylacrylate/methylmethacrylate]
copolymer To a 500 ml round-bottom flask was added 0.3 mole of 9-anthracenemethylacrylate, 0.5 mole of 2-hydroxyethylacrylate, 0.2 mole of methylmethacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylacrylate/2-hydroxyethylacrylate/methylmethacrylate] copolymer of Formula 15. Yield: 81%.

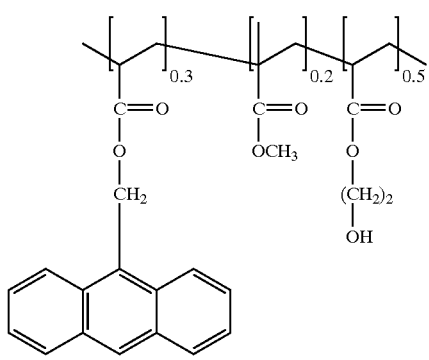

15

EXAMPLE VIII

Synthesis of poly[9-anthracenemethylacrylate/3-hydroxypropylacrylate/methylmethacrylate] copolymer To a 500 ml round-bottom flask was added 0.3 mole of 9-anthracenemethylacrylate, 0.5 mole of 3-hydroxypropylacrylate, 0.2 mole of methylmethacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylacrylate/3-hydroxypropylacrylate/methylmethacrylate] copolymer of Formula 16. Yield: 82%.

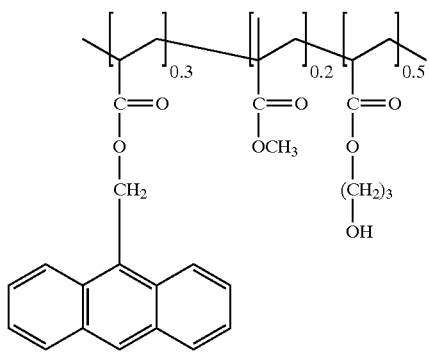

16

EXAMPLE IX

Synthesis of poly[9-anthracenemethylacrylate/4-hydroxybutylacrylate/methylmethacrylate] copolymer To a 500 ml round-bottom flask was added 0.3 mole of 9-anthracenemethylacrylate, 0.5 mole of 4-hydroxybutylacrylate, 0.2 mole of methylmethacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylacrylate/4-hydroxybutylacrylate/methylmethacrylate] copolymer of Formula 17. Yield: 80%.

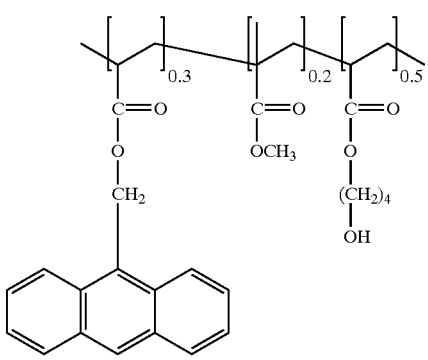

17

EXAMPLE X

Synthesis of poly[9-anthracenemethylmethacrylate/2-hydroxyethylacrylate/methylmethacrylate] copolymer To a 500 ml round-bottom flask was added 0.3 mole of 9-anthracenemethylmethacrylate, 0.5 mole of 2-hydroxyethylacrylate, 0.2 mole of methylmethacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylmethacrylate/2-hydroxyethylacrylate/methylmethacrylate] copolymer of Formula 18. Yield: 82%.

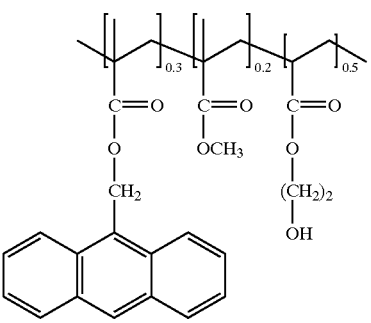

18

EXAMPLE XI

Synthesis of poly[9-anthracenemethylmethacrylate/3-hydroxypropylacrylate/methylmethacrylate] copolymer To a 500 ml round-bottom flask was added 0.3 mole of 9-anthracenemethylmethacrylate, 0.5 mole of 3-hydroxypropylacrylate, 0.2 mole of methylmethacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylacrylate/3-hydroxypropylacrylate/methylmethacrylate] copolymer of Formula 19. Yield: 81%.

19

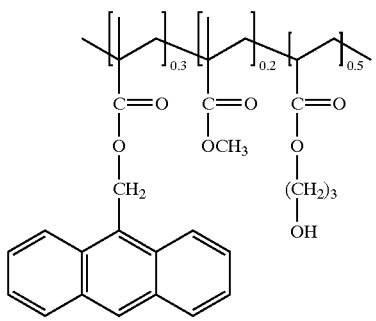

EXAMPLE XII

Synthesis of poly[9-anthracenemethylmethacrylate/
4-hydroxybutylacrylate/methylmethacrylate]
copolymer To a 500 ml round-bottom flask was added 0.3 mole of 9-anthracenemethylmethacrylate, 0.5 mole of 4-hydroxybutylacrylate, 0.2 mole of methylmethacrylate, 300 g of THF, and 0.1–3 g of AIBN. The resulting solution was stirred at 60–75° C. for 5–20 hours under nitrogen atmosphere. The reaction mixture was precipitated in ethyl ether or n-hexane. The precipitate was filtered and dried to provide poly[9-anthracenemethylmethacrylate/4-hydroxybutylacrylate/methylmethacrylate] copolymer of Formula 20. Yield: 80%.

20

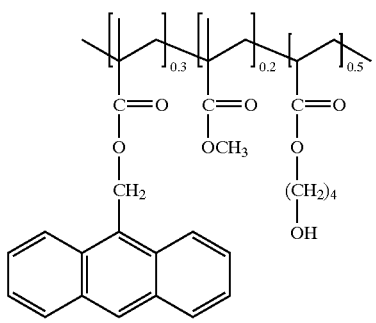

EXAMPLE XIII

Synthesis of polyacrolein polymer

To a 500 ml round-bottom flask was added 0.5 moles of acrolein, 50 g of THF and 0.1–3 g of AIBN. The resulting solution was stirred at 60–75° C. for 5–20 hours under a nitrogen atmosphere. The reaction mixture was precipitated by adding ethyl ether or n-hexane. The precipitate was filtered and dried to provide polyacrolein polymer. Yield: 86%.

Polyacrolein (10 g) was dissolved in methanol and stirred at 80° C. for 24 hours to give poly(acroleinmethylacetal) of Formula 3, where $R^7$ is hydrogen and $R^8$ is methyl. Yield 90%.

EXAMPLE XIV

Preparation of ARC

A polymer of Formula 1 or 2, prepared in any of Examples I to XII, and a polymer of Formula 3, prepared in Example XIII, were dissolved in propyleneglycol methylether acetate (PGMEA). This solution, in combination with 0.1–30% by weight of at least one additive described above, was filtered, coated on a wafer, and hard-baked at 100–300° C. for 10–1,000 sec to form an ARC. A photosensitive material (i.e., photoresist composition) can be applied on the ARC and imaged to form an ultrafine pattern using a submicrolithographic process.

Containing a chromophore, as described heretofore, the ARC of the present invention exhibits excellent absorbance at the wavelengths useful for submicrolithography.

In particular, excellent cross-linking reaction efficiency and storage stability are realized in the present invention. Additionally, the uncured ARC resin of the present invention are soluble in substantially all hydrocarbon solvents, but the cured ARC resin of the present invention is substantially insoluble in most hydrocarbon solvents. Thus, the ARC resin of the present invention can be coated readily onto a substrate, and the resulting cured coating prevents undercutting and footing problems which can occur when forming images on photosensitive materials in the absence of such an ARC coating. Because the ARC polymer (i.e., resin) of the present invention consists of acrylate polymers, the coating layer has higher etching rate than photosensitive films resulting in a high etch selection ratio.

ARCs of the present invention are useful in forming an ultrafine pattern on a substrate using a submicrolithographic process, for example, using KrF (248 nm) or ArF (193 nm) lasers as light sources. ARCs of the present invention allow formation of stable ultrafine patterns that are suitable for 64M, 256M, 1G, 4G and 16G DRAM semiconductor devices and greatly improves the production yield of these devices.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An anti-reflective coating composition suitable for use in fabrication of semiconductor devices, comprising a polymer of the formula:

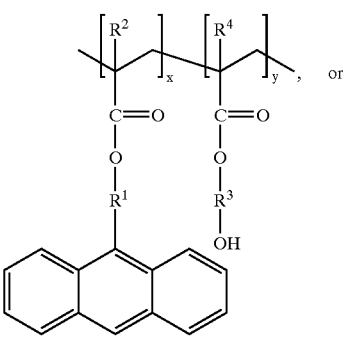

-continued

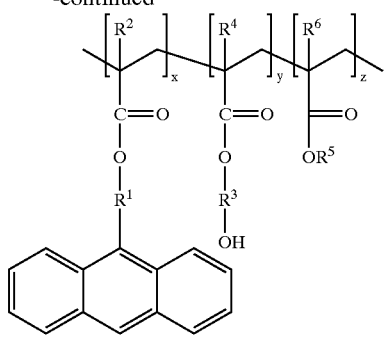

and an acetal polymer of the formula:

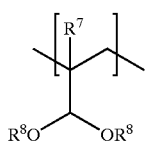

wherein each of $R^1$ and $R^3$ is independently $C_1$–$C_5$ alkylene;

each of $R^2$, $R^4$, $R^6$, and $R^7$ is independently hydrogen or alkyl;

each of $R^5$ and $R^8$ is independently alkyl; and x, y and z are mole fractions, each of which is in the range of from about 0.01 to about 0.99.

2. The anti-reflective coating composition of claim 1, further comprising an additive selected from the group consisting of anthracene, 9-anthracenemethanol, 9-anthracenecarbonitrile, 9-anthracenecarboxylic acid, dithranol, 1,2,10-anthracenetriol, anthraflavonic acid, 9-anthraldehydeoxime, 9-anthraldehyde, 2-amino-7-methyl-5-oxo-5H-[1]benzopyrono[2,3-b]pyridine-3-carbonitrile, 1-aminoanthraquinone, anthraquinone-2-carboxylic acid, 1,5-dihydroxyanthraquinone, anthrone, 9-anthryltrifluoromethyl ketone, 9-alkylanthracene derivative of the formula:

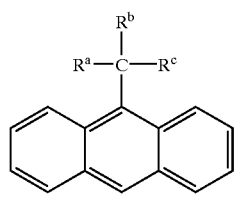

9-carboxylanthracene derivative of the formula:

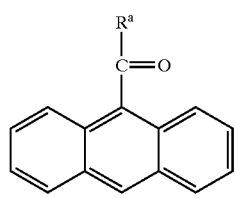

1-carboxylanthracene derivative of the formula 6:

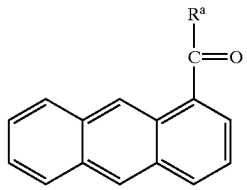

and mixtures thereof,
wherein
each of $R^a$, $R^b$, and $R^c$ is independently hydrogen, hydroxy, hydroxyalkyl, optionally substituted $C_1$–$C_5$ alkyl, or alkoxyalkyl.

3. A method for producing an anti-reflective polymer coated substrate comprising the steps of:
(a) coating an anti-reflective coating composition on a substrate, wherein said anti-reflective coating composition comprises an anti-reflective coating polymer of the formula:

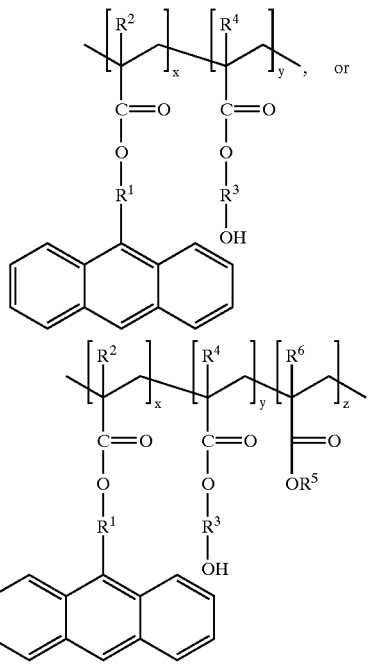

and an acetal polymer of the formula:

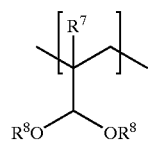

wherein
each of $R^1$ and $R^3$ is independently $C_1$–$C_5$ alkylene;
each of $R^2$, $R^4$, $R^6$, and $R^7$ is independently hydrogen or alkyl;
each of $R^5$ and $R^8$ is independently alkyl; and
x, y and z are mole fractions, each of which is in the range of from about 0.01 to about 0.99; and
(b) curing said anti-reflective coating polymer by heating said coated substrate to temperature in the range of from about 100° C. to about 300° C. to produce said anti-reflective coating coated substrate.

4. The method of claim 3, wherein said anti-reflective coating composition further comprises an additive selected from the group consisting of anthracene, 9-anthracenemethanol, 9-anthracenecarbonitrile, 9-anthracenecarboxylic acid, dithranol, 1,2,10-anthracenetriol, anthraflavonic acid, 9-anthraldehydeoxime, 9-anthraldehyde, 2-amino-7-methyl-5-oxo-5H-[1]benzopyrono[2,3-b]pyridine-3-carbonitrile, 1-aminoanthraquinone, anthraquinone-2-carboxylic acid, 1,5-dihydroxyanthraquinone, anthrone, 9-anthryltrifluoromethyl ketone, 9-alkylanthracene derivative of the formula:

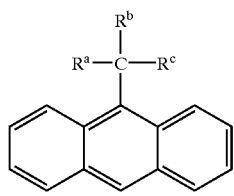

9-carboxylanthracene derivative of the formula:

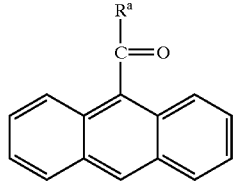

1-carboxylanthracene derivative of the formula 6:

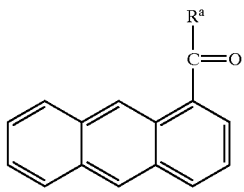

and mixtures thereof,
wherein
each of $R^a$, $R^b$, and $R^c$ is independently hydrogen, hydroxy, hydroxyalkyl, optionally substituted $C_1$–$C_5$ alkyl, or alkoxyalkyl.

5. The method of claim 3 further comprising the steps of producing said anti-reflective coating composition, wherein said anti-reflective coating composition producing step comprises
(i) admixing said anti-reflective coating polymer with an organic solvent; and
(ii) filtering said admixture.

6. The method of claim 5, wherein said organic solvent is selected from the group consisting of ethyl 3-ethoxypropionate, methyl 3-methoxypropionate, cyclohexanone, and propylene glycol methyletheracetate.

7. A semiconductor device comprising an anti-reflective polymer coated substrate produced by a method of claim 3.

8. An ARC composition comprising an acrylate derivative polymer having a chromophore group that has a high absorption of deep UV radiation, and a poly[acroleinalkylacetal] polymer of the formula:

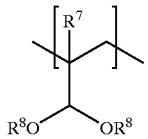

wherein
$R^7$ is hydrogen or methyl; and
$R^8$ is methyl.

* * * * *